United States Patent [19]

Obitsu et al.

[11] Patent Number: 5,223,176
[45] Date of Patent: Jun. 29, 1993

[54] ZIRCONIA SOL AND METHOD FOR MAKING THE SAME

[75] Inventors: Masamichi Obitsu; Takao Kaga; Yasuhiro Fujii, both of Funabashi, Japan

[73] Assignee: Nissan Chemical Industries, Ltd., Tokyo, Japan

[21] Appl. No.: 829,583

[22] Filed: Feb. 3, 1992

Related U.S. Application Data

[63] Continuation of Ser. No. 415,109, Sep. 29, 1989, abandoned.

[30] Foreign Application Priority Data

Sep. 30, 1988 [JP] Japan ................ 63-248441

[51] Int. Cl.$^5$ .............................. C01G 25/02
[52] U.S. Cl. ...................... 252/313.1; 106/286.4; 106/450; 252/363.5; 423/608; 501/103
[58] Field of Search .................. 252/313.1, 363.5; 106/450, 286.4; 423/608; 501/103

[56] References Cited

U.S. PATENT DOCUMENTS

| | | | |
|---|---|---|---|
| 2,013,856 | 9/1935 | Kinzie | 106/450 R |
| 2,952,580 | 9/1960 | Freud et al. | 162/158 |
| 2,984,576 | 5/1961 | Alexander et al. | 106/450 X |
| 2,984,628 | 5/1961 | Alexander et al. | 252/313.1 |
| 3,298,957 | 1/1967 | Gens | 252/182.29 |
| 3,514,252 | 5/1970 | Levy, Jr. et al. | 106/450 X |
| 3,741,782 | 6/1973 | Stewart et al. | 252/351 X |
| 3,966,502 | 6/1976 | Binns | 106/450 X |
| 4,612,138 | 9/1986 | Keiser | 252/313.2 |
| 5,055,442 | 10/1991 | Osaka et al. | 502/439 |

FOREIGN PATENT DOCUMENTS

| | | |
|---|---|---|
| 0199930 | 4/1986 | European Pat. Off. . |
| 1114001 | 11/1954 | France . |
| 2088550 | 7/1972 | France . |
| 58-79818 | 5/1983 | Japan . |
| 59-107969 | 6/1984 | Japan . |
| 60-176920 | 9/1985 | Japan . |
| 61-201622 | 9/1986 | Japan . |
| 62-162626 | 7/1987 | Japan . |

OTHER PUBLICATIONS

Derwent Abstract, WPI Acc. No. 89-244343/34, *Toray Ind. Inc.*, JP 1176225 Jul. 1989.
Webster's II New Riverside Dictionary, (1988) Houghton Mifflin Co., Boston, MA, p. 1105.
Van Nostrand's Scientific Encyclopedia, (1968) D. Van Nostrand Co., Inc., Princeton, N.J. p. 1645.
Merck Index, Tenth Edition, (1983), M. Windholz et al., eds., Merck & Co., Inc. Rahway, N.J., p. 1460, entry No. 9985.

*Primary Examiner*—Robert L. Stoll
*Assistant Examiner*—John M. Covert
*Attorney, Agent, or Firm*—Birch, Stewart, Kolasch & Birch

[57] ABSTRACT

A stable basic zirconia sol can be prepared by adding to an acidic aqueous zirconia sol a dispersion stabilizer selected from the group consisting of a water-soluble organic acid having a hydroxyl group and a water-soluble organic compound having at least two hydroxyl groups, and thereafter adjusting the sol with a basic compound to pH 6 to 14.

13 Claims, No Drawings

ZIRCONIA SOL AND METHOD FOR MAKING THE SAME

This application is a continuation of application Ser. No. 07/415,109 filed on Sept. 29, 1989, now abandoned.

This invention relates to zirconia sol with pH 6 to 14 for use as stock material for the preparation of ceramic materials and electronic materials for sensors and other electronic parts, coating agents, and binders for precision casting.

BACKGROUND OF THE INVENTION

Few zirconia sols are known in the art which are stable at a basicity of pH 6 or higher. Most well-known conventional aqueous zirconia sols are acidic ones having an acidity of lower than pH 6. Methods for preparing such aqueous zirconia sols are known from U.S. Pat. No. 2,984,628 and Japanese Patent Application Kokai No. 79818/1983, for example. These sols are used in numerous applications as binders for assisting shaping of various refractory materials, coating agents for impregnation and coating purposes, agents useful in shaping of inorganic fibers such as ceramic fibers, shaping of molds for precision casting, and surface treatment of fibers, abrasives, micro-fillers and the like.

Although it has been recently recognized useful to use zirconia sols for the manufacture of ceramic and electronic materials, conventional well-known acidic zirconia sols at a pH level of lower than 6 have a problem of corrosion. In addition, acidic zirconia sol tends to lose its stability when a stabilizing agent, for example, yttrium oxide, magnesium oxide, and calcium oxide is added to the zirconia sol for converting zirconia into stabilized or partially stabilized zirconia. It is thus difficult to homogeneously disperse the stabilizer in zirconia sol.

Most organic binders used as shaping aids for ceramics are either nonionic or anionic. However, the use of an acidic zirconia sol dictates the use of a cationic binder, limiting the type and number of available binders.

The above-mentioned problems of acidic zirconia sol at a pH level of lower than 6 would be solved if basic zirconia sols could be available. However, mere addition of a basic substance to a conventional acidic zirconia sol causes agglomeration.

Therefore, an object of the present invention is to provide a stable zirconia sol at pH 6.14 and a method for preparing the same.

SUMMARY OF THE INVENTION

According to one form of the present invention, there is provided a zirconia sol comprising zirconia in water and a dispersion stabilizer selected from the group consisting of a water-soluble organic acid having a hydroxyl group and a water-soluble organic compound having at least two hydroxyl groups, the sol being at pH 6 to 14.

According to another form of the present invention, there is provided a method for preparing a zirconia sol comprising the steps of adding to an acidic aqueous zirconia sol a dispersion stabilizer selected from the group consisting of a water-soluble organic acid having a hydroxyl group and a water-soluble organic compound having at least two hydroxyl groups, and thereafter adjusting the sol with a basic compound to pH 6 to 14.

DETAILED DESCRIPTION OF THE INVENTION

The acidic aqueous zirconia sols from which the zirconia sol of the invention is prepared have a pH value of lower than 6, preferably from 0.5 to 5.5 and are selected from well-known zirconia sols. The zirconia concentration in the sols may preferably be in the range of from about 5% to about 50% by weight, more preferably from about 10% to about 30% by weight. Included are such acidic zirconia sols as disclosed in U.S. Pat. No. 2,984,628 involving heating an aqueous solution of zirconium oxychloride for hydrolysis to form zirconia sol, Japanese Patent Application Kokai Nos. 79818/1983, 107969/1984, 176920/1985, 201622/1986, and 162626/1987.

The dispersion stabilizer added to the acidic zirconia sol according to the invention is selected from the group consisting of a water-soluble organic acid having a hydroxyl group and a water-soluble organic compound having at least two hydroxyl groups. Examples of the water-soluble organic acid having a hydroxyl group include lactic acid, malic acid, citric acid, tartaric acid, salicylic acid, and sulfosalicylic acid. Examples of the water-soluble organic compound having at least two hydroxyl groups include ethylene glycol, propylene glycol, disodium 4,5-dihydroxy. 1,3-benzenedisulfonate (trade name: Tiron), glycerin, polyvinyl alcohol, and hydroquinone.

The dispersion stabilizer is preferably added in an amount of at least 5%, more preferably from 5 to 50%, most preferably from 10 to 30% based on the weight of the zirconia, that is, zirconium oxide $ZrO_2$. It is essential for the dispersion stabilizer to be completely dissolved in the acidic sol.

After the dispersion stabilizer is added to the acidic zirconia sol, a basic substance is added to adjust the sol to pH 6 or higher. The basic substances used herein include water-soluble inorganic bases such as sodium hydroxide, potassium hydroxide, lithium hydroxide, and ammonia; and water-soluble organic bases, for example, amines such as n-propylamine, monoethanolamine, and triethanolamine; quaternary ammonium hydroxides such as monomethyltriethyl. ammonium hydroxide and trimethylbenzylammonium hydroxide, and guanidine hydroxide.

It is impossible to produce a stable zirconia sol at pH 6 or higher by first adding a basic substance as defined above to an acidic zirconia sol and then adding a dispersion stabilizer as defined above to the sol.

The zirconia sol prepared by the method of the invention often contains chloride ions. If the presence of chloride ions is undesirable, the ions can be readily removed by ultrafiltration or ion exchange. The zirconia sol of the invention is stable independent of whether chloride ions are present or absent. The zirconia sol of the invention has a zirconia concentration in the range of from about 5% to about 50% by weight, more preferably from about 10% to about 30% by weight. The sol is at pH 6.14 and preferably has a lower pH limit of 7 and an upper pH limit of 12.

Once the zirconia sol at pH 6 or higher is established according to the present invention, it remains stable. The addition of a stabilizing agent for zirconia, for example, yttrium oxide, magnesium oxide, and calcium oxide to the zirconia sol does cause no agglomeration of the sol, the sol remaining stable, thus yielding partially and fully stabilized species of zirconia having improved properties.

In addition, the addition of a nonionic or anionic organic binder to the zirconia sol of the invention does cause no agglomeration of the sol, ensuring that the sol is eventually formed into a thin film which is constructed of partially stabilized zirconia.

The zirconia sol of the invention is useful as a binder for precision casting.

EXAMPLE

Examples of the invention are given below by way of illustration and not by way of limitation. All percents are by weight unless otherwise stated.

EXAMPLES 1-8

To 200 grams of a zirconia sol acidified with hydrochloric acid having a zirconia concentration of 20%, a mean particle diameter of 500 Å, and pH 4 (prepared by the method of Japanese Patent Application Kokai No. 79818/1983) at room temperature were added 145.7 grams of water and 40 grams of a 10% citric acid aqueous solution. Thereafter, 14.3 grams of 28% aqueous ammonia was added to the sol. There was obtained a zirconia sol containing 10% of zirconia, 1% of citric acid, 1% of ammonia at pH 10.1.

The resulting zirconia sol remained stable after it was allowed to stand for one month at 40° C.

This basic zirconia sol was refined by ultrafiltration. That is, 400 grams of the basic zirconia sol was washed with 1,200 grams of 1% aqueous ammonia using a ultrafiltration equipment with a ultrafiltration membrane having a fraction al molecular weight of 200,000. Subsequent concentration yielded a basic zirconia sol containing 20% of zirconia, 1.4% of citric acid, and 20 ppm of Cl at pH 10.2.

A series of basic zirconia sols were obtained by repeating the procedure of Example 1 except that the citric acid dispersion stabilizer was replaced by lactic acid, malic acid, and tartaric acid. Another series of basic zirconia sols were obtained by repeating the procedure of Example 1 except that the ammonia was replaced by the basic compounds shown in Table 1. The physical properties of these basic zirconia sols, which were not refined by ultra. filtration, are shown in Table 1. All these sols showed excellent stability as in Example 1.

TABLE 1

| Example | Dispersion stabilizer | Basic compound | ZrO$_2$ conc. | pH | Specific gravity |
|---|---|---|---|---|---|
| 1 | Citric acid | NH$_4$OH | 10% | 10.1 | 1.11 |
| 2 | Lactic acid | NH$_4$OH | 10% | 10.2 | 1.11 |
| 3 | Malic acid | NH$_4$OH | 10% | 10.2 | 1.11 |
| 4 | Tartaric acid | NH$_4$OH | 10% | 10.2 | 1.11 |
| 5 | Citric acid | NaOH | 10% | 11.5 | 1.11 |
| 6 | Citric acid | KOH | 10% | 11.3 | 1.11 |
| 7 | Citric acid | MEA* | 10% | 10.2 | 1.11 |
| 8 | Citric acid | TMBA** | 10% | 11.3 | 1.11 |

*MEA: monoethanolamine
**TMBA: trimethylbenzylammonium hydroxide

COMPARATIVE EXAMPLE 1

To 200 grams of the same acidic zirconia sol as used in Example 1 were added 14.3 grams of 28% aqueous ammonia at room temperature. The sol agglomerated. Further addition of 145.7 grams of water and 40 grams of a 10% citric acid aqueous solution did not induce peptization. No sol was obtained.

EXAMPLE 9

To 200 grams of the same acidic zirconia sol as used in Example 1 at room temperature were added 181.7 grams of water and 4 grams of ethylene glycol. Thereafter, 14.3 grams of 28% aqueous ammonia was added to the sol. There was obtained a basic zirconia sol containing 10% of zirconia, 1% of ethylene glycol, 1% of ammonia at pH 10.2.

The resulting zirconia sol remained stable after it was allowed to stand for one month at 40° C.

This basic zirconia sol was refined with an ion exchange resin. That is, 400 grams of the basic zirconia sol was passed through a column charged with 500 c.c. of a cation exchange resin (trade name, Diaion SA-11A manufactured by Mitsubishi Chemical Industries Ltd.). Subsequent concentration yielded a basic zirconia sol containing 17.1% of zirconia, 1.3% of ethylene glycol, and 1,000 ppm of Cl at pH 10.2.

A series of basic zirconia sols were obtained by repeating the procedure of Example 9 except that the ethylene glycol dispersion stabilizer was replaced by propylene glycol, glycerin, and polyvinyl alcohol. All these sols showed excellent stability as in Example 9.

The physical properties of these basic zirconia sols, which were not refined by ion exchange, are shown in Table 2.

TABLE 2

| Example | Dispersion stabilizer | ZrO$_2$ Conc. | pH | Specific gravity |
|---|---|---|---|---|
| 9 | Ethylene glycol | 10% | 10.1 | 1.12 |
| 10 | Propylene glycol | 10% | 10.2 | 1.12 |
| 11 | Glycerin | 10% | 10.2 | 1.12 |
| 12 | Polyvinyl alcohol | 10% | 10.2 | 1.12 |

EXAMPLE 13

To 200 grams of the basic zirconia sol refined by ultrafiltration in Example 1 was added 2.27 grams of yttria powder (manufactured by Mitsuwa Kagaku Yakuhin K. K.), the amount of yttria corresponding to 3 mol% based on the zirconia. As opposed to the agglomeration found with an acidic zirconia sol having yttria added, the basic zirconia sol maintained a stable sol state without agglomeration.

The resulting sol was removed of the water with an evaporator and heated at 800° C. for 30 minutes, obtaining zirconia powder. An x-ray diffraction analysis showed that the power was tetragonal zirconia.

In another run, 8.15 grams of yttria powder was added to 200 grams of the basic zirconia sol refined by ultra filtration in Example 1, the amount of yttria corresponding to 10 mol% based on the zirconia. There was obtained a similarly stable sol. The sol was converted into a powder in the same manner as above, obtaining cubic zirconia.

Similarly, stable sols were obtained by adding calcium oxide, magnesium oxide, and cerium oxide instead of the yttria in amounts of 3 to 10 mol% based on the zirconia.

EXAMPLE 14

In the procedure of Example 13, the yttria by 2.81 and 10.1 grams of yttrium hydroxide, the amounts of yttrium hydroxide corresponding to 3 and 10 mol% of yttrium oxide based on the zirconia.

The basic zirconia sols maintained a stable sol state without agglomeration. The resulting sols were removed of the water with an evaporator and heated at 400° C. for 30 minutes, obtaining zirconia powders. An x-ray diffraction analysis showed that the powers were tetragonal zirconia when the yttrium oxide content was 3 mol% and cubic zirconia when the yttrium oxide content was 10 mol%.

Similarly, stable sols were obtained by adding calcium hydroxide, magnesium hydroxide, and cerium hydroxide instead of the yttria in amounts of 3 to 10 mol% based on the zirconia.

EXAMPLE 15

To 200 grams of the basic zirconia sol refined by ultrafiltration in Example 1 was added 4 grams of an anionic emulsion type organic binder (trade name, DM60 manufactured by Hoechst Gosei K. K.). As opposed to the fact that an acidic zirconia sol agglomerated when this binder was added thereto, the basic zirconia sol of Example 1 remained stable without agglomeration. The sol having the binder added thereto was coated on a film of polyethylene terephthalate and dried into a thin layer, obtaining an organic film having zirconia borne thereon.

EXAMPLE 16

To the zirconia sol containing 3 mol% of yttria based on the amount of zirconia prepared in Example 13 was added .4 grams of an emulsion type organic binder (DM60 manufactured by Hoechst Gosei K. K.). The sol was then coated on a film of polyethylene terephthalate and dried into a thin layer, obtaining an organic film having yttria and zirconia borne thereto. After low burnout of organics at 400° C., the coated film was sintered at 1,400° C., obtaining a thin film of partially stabilized zirconia which was 3 cm by 3 cm by 30 μm thick and had a density of 6.08 g/cm$^3$.

EXAMPLE 17

The basic zirconia sol refined in Example 1 was further concentrated by ultrafiltration into a zirconia sol concentrate containing 30% by weight of $ZrO_2$ at pH 10.1.

Using the sol concentrate as a binder, a precision casting mold was fabricated by a lost-wax process.

The original pattern used was a brass plate of 20 mm by 150 mm coated with wax. A slurry was prepared from the zirconia sol concentrate as shown in Table 3, the slurry being found to remain stable after 3 month shelf storage. The original pattern was immersed in the slurry. The surface of the pattern which had been immersed in the slurry was sanded with a stucco in the form of a particulate refractory material as identified in Table 4 and then dried at 23° C. and RH 56% for the time shown in Table 4. The procedure from slurry immersion to drying was repeated 6 times. Finally the pattern was immersed in the slurry and dried. After the final drying, the pattern was heated using a gas burner to remove the plate, obtaining a green mold without disintegration or a crack.

The green mold was fired for one hour in an electric furnace at 1400° C., obtaining a fired mold. The fired mold was devoid of any deformation or defect and satisfactory for practical casting purposes as demonstrated by a bending strength of 60 kg/cm$^2$.

TABLE 3

| Ingredients | Slurry composition Application 1st–2nd | Slurry composition Application 3rd–7th |
|---|---|---|
| Zirconia sol | 900 g | 900 g |
| Filler*[1] | 3560 g | 3460 g |
| Organic binder*[2] | 100 g | 100 g |
| Surface-active agent*[3] | 7 ml | 7 ml |
| Defoaming agent*[4] | 1 ml | 1 ml |

*[1]Filler: electrofused zirconia (tradename Zirbon GA, 325 mesh, manufactured by Fukushima Seiko K.K.)
*[2]Organic binder: tradename DM-60 manufactured by Hoechst Gosei K.K.
*[3]Surface-active agent: tradename Victorwet manufactured by Stauffer Chemical
*[4]Defoaming agent: tradename SN-Defoamer 5016 manufactured by San Nopco Ltd.

TABLE 4

| Layer | Stucco and Drying Time Stucco | Drying time |
|---|---|---|
| 1st | Electrofused zirconia*[1] | 3 hours |
| 2nd | Electrofused zirconia | 3 hours |
| 3rd | Electrofused alumina*[2] | 3 hours |
| 4th | Electrofused alumina | 12 hours |
| 5th | Electrofused alumina | 3 hours |
| 6th | Electrofused alumina | 3 hours |
| 7th | — | 48 hours |

*[1]tradename Zirbon GA, 42–100 mesh, manufactured by Fukushima Seiko K.K.
*[2]tradename Nikkei Random, 14 mesh, manufactured by Nikkei Kako K.K.

Although some preferred embodiments have been described, many modifications and variations may be made thereto in the light of the above teachings. It is therefore to be understood that within the scope of the appended claims, the invention may be practiced otherwise than as specifically described.

We claim:

1. An aqueous zirconia sol at pH 6 to 14 containing a dispersion stabilizer selected from the group consisting of a water-soluble organic acid having a hydroxyl group and a water-soluble organic compound having at least two hydroxyl groups, and water.

2. The aqueous zirconia sol of claim 1 wherein said dispersion stabilizer is present in an amount of at least 5% based on the weight of zirconia in the zirconia sol.

3. The aqueous zirconia sol of claim 1 or 2 wherein said dispersion stabilizer is selected from the group consisting of lactic acid, malic acid, citric acid, tartaric acid, ethylene glycol, propylene glycol, glycerin, and polyvinyl alcohol.

4. A method for preparing a zirconia sol comprising the steps of:

adding to an acidic aqueous zirconia sol a dispersion stabilizer selected from the group consisting of a water-soluble organic acid having a hydroxyl group and a water-soluble organic compound having at least two hydroxyl groups, and thereafter adjusting the sol with a basic compound to pH 6 to 14.

5. The method of claim 4 wherein said dispersion stabilizer is added in an amount of at least 5% based on the weight of zirconia in said zirconia sol.

6. The method of claim 4 or 5 where said dispersion stabilizer is selected from the group consisting of lactic acid, malic acid, citric acid, tartaric acid, ethylene glycol, propylene glycol, glycerin, and polyvinyl alcohol.

7. An aqueous sol having a zirconia concentration of from about 5% to about 50% by weight of the sol, wherein said zirconia sol contains water and a dispersion stabilizer selected from the group consisting of a water-soluble organic acid having a hydroxyl group and a water-soluble organic compound having a least two hydroxyl groups in an amount of from 5 to 50% by weight of zirconia in the sol, and has a pH of 6 to 14.

8. The zirconia sol of claim 7, wherein said zirconia concentration is from about 10% to about 30% by weight of the sol, and wherein said dispersion stabilizer is present in an amount from 10 to 30% based on the weight of said zirconia.

9. The zirconia sol of claim 7 or 8, wherein said dispersion stabilizer is selected from the group consisting of lactic acid, malic acid, citric acid, tartaric acid, ethylene glycol, propylene glycol, glycerin, and polyvinyl alcohol.

10. A method for preparing a zirconia sol having a pH of 6 to 14 comprising the steps of:

adding to an acidic aqueous zirconia sol having a zirconia concentration of about 5% to about 50% by weight of the sol and a pH of lower than 6 a dispersion stabilizer selected from the group consisting of a water-soluble organic acid having a hydroxyl group and a water-soluble organic compound having at least two hydroxyl groups, and thereafter adjusting the sol with a basic compound to pH 6 to 14.

11. The method of claim 10, wherein said zirconia concentration is from about 10% to about 30% by weight of the sol, and wherein said dispersion stabilizer is present in an amount from 10 to 30% based on the weight of said zirconia.

12. The method of claim 10 or 11, wherein said dispersion stabilizer is selected from the group consisting of lactic acid, malic acid, citric acid, tartaric acid, ethylene glycol, propylene glycol, glycerin, and polyvinyl alcohol.

13. The aqueous zirconia sol of claim 1, wherein said sol is a liquid colloidal dispersion.

* * * * *